Figure 1:
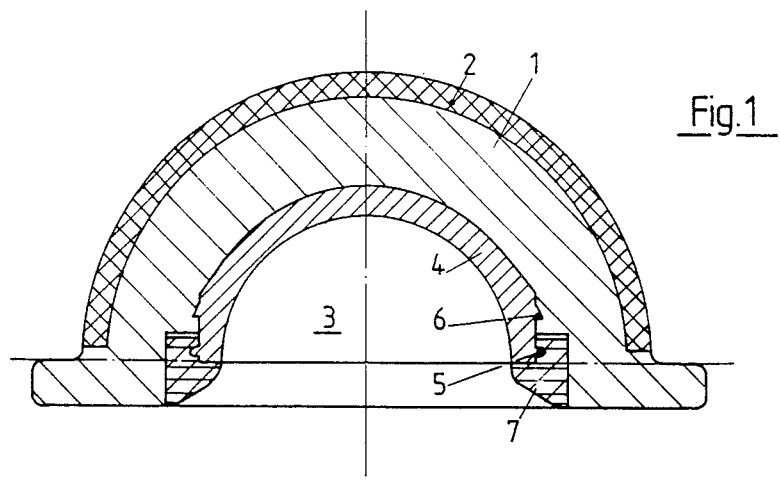

United States Patent [19]

Frey et al.

[11] Patent Number: 4,969,910
[45] Date of Patent: Nov. 13, 1990

[54] ACETABULAR CUP PROSTHESIS

[75] Inventors: Otto Frey, Winterthur; Roland Willi, Stadel, both of Switzerland

[73] Assignee: Sulzer Berothers Limited, Winterthur, Switzerland

[21] Appl. No.: 257,285

[22] Filed: Oct. 13, 1988

[30] Foreign Application Priority Data

Nov. 11, 1987 [CH] Switzerland .................. 04398/87

[51] Int. Cl.$^5$ .............................................. A61F 2/34
[52] U.S. Cl. ...................................................... 623/22
[58] Field of Search .................. 623/16, 18, 20, 22, 623/23

[56] References Cited

U.S. PATENT DOCUMENTS

| 4,479,271 | 10/1984 | Bolesky et al. | 623/20 |
| 4,624,674 | 11/1986 | Pappas et al. | 623/22 |
| 4,687,487 | 8/1987 | Hintermann | 623/22 |

FOREIGN PATENT DOCUMENTS

| 0053794 | 6/1982 | European Pat. Off. | 623/22 |
| 0119321 | 9/1984 | European Pat. Off. | |
| 0234811 | 9/1987 | European Pat. Off. | |
| 0235606 | 9/1987 | European Pat. Off. | 623/22 |
| 2024583 | 11/1970 | Fed. Rep. of Germany | 623/22 |
| 2551655 | 3/1985 | France. | |

Primary Examiner—David J. Isabella
Attorney, Agent, or Firm—Kenyon & Kenyon

[57] ABSTRACT

The acetabular cup prosthesis has a metal socket having a socket shell for receiving a spherical joint head as well as a plastic ring which covers the equatorial edge surface of the metal socket and which has an inner diameter corresponding to the inner diameter of the shell. In the event of a dislocation of the joint head, the polished surface of the joint head contacts the plastic ring to deform the ring without imposing a point load on the metal joint head.

11 Claims, 1 Drawing Sheet

ACETABULAR CUP PROSTHESIS

This invention relates to an acetabular cup prosthesis.

Heretofore, various types of acetabular cup prostheses have been known for implantation in a pelvic bone. At the present time, total prostheses have been constructed with pairs of rubbing surfaces in which a metal joint head is mounted in a socket shell which is also in the form of a polished metal surface because of the good sliding properties provided by such surfaces. Examples of acetabular cup prostheses having metal cups or sockets in which a shell is fashioned are described in German Patent No. 3446048 and U.S. patent application Ser. No. 07/204,108.

In the "normal operation" of such a total prosthesis, the pressures which exist between the joint head and the socket shell are distributed over relatively large zones of the surfaces of the two elements. However, in the event of dislocations in which the joint head is "dislocated" from the socket shell, the spherical surface experiences very limited linear or point loads locally which may easily damage the polished spherical surface.

Accordingly, it is an object of the invention to reduce the risk of damage to a metal joint head surface in the event of a dislocation in a polished metal socket shell.

It is another object of the invention to dissipate a local load peak in an acetabular cup prosthesis caused by a dislocation of a joint head.

Briefly, the invention provides an acetabular cup prosthesis which is comprised of a metal socket having a socket shell for receiving a joint head and an equatorial edge surface as well as a plastic ring which is disposed over the equatorial edge surface of the socket with an inner diameter of the ring corresponding to an inner diameter of the shell.

The plastic ring which is of a material relatively softer than the metal socket ensures that the spherical surface of a joint head is not attacked and damaged by local load peaks, particularly when subjected to point loads as a result of a dislocation of the joint head.

Conveniently, in order to reduce damage of the plastic ring as far as possible and to assist automatic replacement, that is, "jumping back", of a dislocated joint head into the socket shell, the inner surface of the plastic ring widens outwardly of the shell, that is, the inner diameter of the ring widens outwardly.

Very advantageously, the metal socket can be introduced into a plastic main member having a multi-layer wire mesh in an opposite side to define a porous surface for tissue ingrowth or embedment in bone cement. However, the plastic main member can also be introduced into a metal shell which is operative as an impact damping element.

In order to simplify the construction of the connection between the plastic ring and the metal socket, the plastic main member has a circumferential recess receiving the plastic ring while the plastic ring is snap-fitted externally onto the metal socket. The socket may also be snap-fitted into the plastic main member.

In order to prevent body fluid from penetrating into gaps between the plastic ring and the metal socket or the main member respectively, the outer envelope of the plastic ring and/or the mating surface of the main member is made conical. That is, at least one of the plastic ring and the main member has a conically shaped annular surface foor deformable mounting of the plastic ring in the member.

Figure 2:
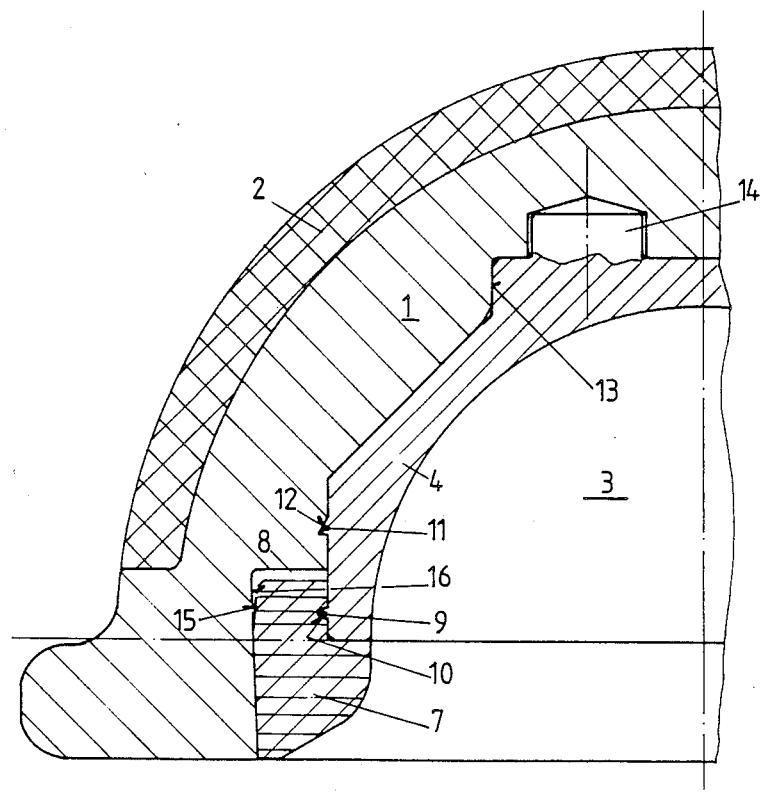

These and other objects and advantages of the invention will become more apparent from the following detailed description taken in conjunction with the accompanying drawings wherein:

FIG. 1 illustrates a cross sectional view of an acetabular cup prosthesis constructed in accordance with the invention; and FIG. 2 illustrates an enlarged view of a part of the cross section of the prosthesis of FIG. 1.

Referring to FIG. 1, the acetabular cup prosthesis has a plastic main member 1 formed with a hemispherical outside surface which is covered by a multi-layer porous wire mesh 2. The wire mesh 2 serves to define a porous surface for anchorage, for example either for the invasion of bone tissue from a pelvic bone or for a mechanical joining to a joint cement bed within a surgically prepared pelvic bone.

The prosthesis also has a metal socket 4 which is received within the plastic main member, for example by means of a snap-fastening 6 and which has a socket shell 3 for receiving a metal joint head (not shown) of a femur head prosthesis. In addition, a plastic ring 7 is disposed over the metal socket 4 and is snap-fitted externally onto the metal socket 4 by a snap fastening 5.

Referring to FIG. 2, the shell 3 is of hemispherical shape while the metal socket 4 has an equatorial edge surface over which the plastic ring 7 is disposed. In addition, the plastic ring 7 has an inner diameter corresponding to the inner diameter of the shell 3 thereby providing a smooth continuity between the inside surfaces of the shell 3 and ring 7. As indicated, the inner surface of the ring 7 widens outwardly of the shell 3. To this end, the inner surface of the ring 7 first widens on a convex curve, than rectilinearly during advancement outwards from the shell 3 until forming the outer closure of the shell 3 in which the joint head bears in the event of a dislocation.

The plastic main member 1 has a circumferential recess 8 receiving the plastic ring 7 such that a portion of the ring 7 lies within the recess 8 between the metal socket 4 and the plastic member 1. In addition, the snap-fastening 5 which is defined by an annular projection 9 on the outside of the metal socket 4 and a corresponding groove 10 in the ring 7 is disposed within the confines of the recess 8.

As also indicated in FIG. 2, the snap-fastening 6 for the metal socket 4 within the main member 1 includes an annular projection 11 on the metal socket 4 and a corresponding annular recess 12 within the main member 1.

The metal socket 4 is also provided with a cylindrical guide 13 in an apex zone of the socket 4 or main member 1 in order to prevent the socket 4 from tilting relative to the main member 1 when being pressed in to the main member 1. In order to secure the socket 4 and member 1 against rotation, the apex zone is also provided with a pin or the like 14 which projects from the socket 4 into a matching bore in the main member 1.

In order to prevent any penetration of body fluid into the recess 8 of the main member 7, the plastic ring 7 and/or the recess 8 is provided with a conically shaped annular surface 15, 16, respectively, for deformable mounting of the plastic ring 7 in the main member 7. That is, the conicity of the annular surface is such that the plastic ring 7 deforms inwardly upon being inserted into the main member 7 so as to produce a press fit relationship over some height of the ring 7.

During the assembly of the prosthesis, the plastic ring 7 is first snap-fitted over the metal socket 4. Thereafter, both are pressed together into the plastic main member 1 until the snap fastening 6 catches.

Instead of constructing the prosthesis with a separate main member 1 and a separate socket 4, the prosthesis may also have a shell 3 disposed directly in a socket which can, if required, have an anchorage ring or an outer shell extending around the exterior.

When in use, should a dislocation of a joint head take place, the joint head may bear on the plastic ring 7 which, being relatively soft, deforms under any localized point load so that the spherical surface of the joint head is not subjected to a local load peak.

The invention thus provides an acetabular cup prosthesis which reduces the risk of damage to a joint head surface in the event of a dislocation of the joint head within the prosthesis.

What is claimed is:

1. An acetabular cup prosthesis comprising
a plastic main member having a hemispherical outside surface;
a metal socket received within said plastic main member and having a socket shell for receiving a metal joint head and an equatorial edge surface recessed within said main member; and
a plastic ring disposed over said equatorial edge surface on said socket with an inner diameter corresponding to an inner diameter of said shell, said ring being received within said member in recessed relation.

2. A prosthesis as set forth in claim 1 wherein said ring has an inner surface which widens outwardly of said shell.

3. A prosthesis as set forth in claim 1 which further comprises a plastic main member receiving said metal socket on one side and a multi-layer wire mesh in an opposite side of said main member to define a porous surface for anchorage.

4. A prosthesis as set forth in claim 3 wherein said plastic main member has a circumferential recess receiving said plastic ring and said plastic ring is snap-fitted onto said metal socket.

5. A prosthesis as set forth in claim 4 wherein said socket is snap-fitted into said plastic main member.

6. A prosthesis as set forth in claim 3 wherein at least one of said plastic ring and said main member has a conically shaped annular surface and said plastic ring is deformally mounted in said member.

7. In an acetabular cup prosthesis the combination comprising
a plastic main member;
a metal socket received within said main member and having a socket shell defining a hemispherical surface for receiving a spherical joint head and an equatorial edge surface recessed within said main member; and
a plastic ring disposed over said equatorial edge surface of said socket and within said main member, said ring having an inner surface extending from said hemispherical surface on a diameter corresponding to an inner diameter of said shell.

8. The combination as set forth in claim 7 wherein said inner surface of said ring widens outwardly of said shell.

9. The combination as set forth in claim 7 wherein said plastic main member has a circumferential recess receiving said plastic ring and wherein said plastic ring is snap-fitted onto said metal socket.

10. The combination as set forth in claim 9 wherein said socket is snap-fitted into said plastic main member.

11. The combination as set forth in claim 9 wherein at least one of said plastic ring and said main member has a conically shaped annular surface and said plastic ring is deformably mounted in said member.

* * * * *

UNITED STATES PATENT AND TRADEMARK OFFICE
CERTIFICATE OF CORRECTION

PATENT NO. : 4,969,910
DATED : November 13, 1990
INVENTOR(S) : OTTO FREY, et al It is certified that error appears in the above-identified patent and that said Letters Patent is hereby corrected as shown below:

```
Column 1, line 67 change "foor" to -for
Column 2, line 61 change "main member 7" to -main member 1-
Column 2, line 64 change "main member 7" to -main member 1-
Column 2, line 67 change "main member 7" to -main member 1-
Column 4, line 12 change "deformally" to -deformably-
```

Signed and Sealed this

Seventh Day of July, 1992

Attest:

DOUGLAS B. COMER

*Attesting Officer*   Acting Commissioner of Patents and Trademarks